United States Patent [19]

Katzir

[11] Patent Number: 5,058,982
[45] Date of Patent: Oct. 22, 1991

[54] ILLUMINATION SYSTEM AND INSPECTION APPARATUS INCLUDING SAME

[75] Inventor: Yigal Katzir, Holon, Israel

[73] Assignee: Orbot Systems Ltd., Israel

[21] Appl. No.: 565,489

[22] Filed: Aug. 10, 1990

Related U.S. Application Data

[63] Continuation-in-part of Ser. No. 370,064, Jun. 21, 1989, which is a continuation of Ser. No. 150,332, Jan. 29, 1988, abandoned.

[51] Int. Cl.$^5$ .............................................. G02B 6/32
[52] U.S. Cl. ........................................ 385/33; 385/15; 385/901
[58] Field of Search ............................ 350/96.15, 96.18

[56] References Cited

U.S. PATENT DOCUMENTS

| | | | |
|---|---|---|---|
| 804,996 | 11/1905 | Anthony | 350/537 |
| 2,257,881 | 10/1941 | Jaros | 240/1 |
| 2,852,693 | 9/1958 | Hughes et al. | 250/71 |
| 3,229,564 | 1/1966 | Meltzer | 356/446 |
| 3,251,984 | 5/1966 | Colterjohn | 240/1.3 |
| 3,270,194 | 8/1966 | Lee | 240/20 |
| 3,277,773 | 10/1966 | White | 88/14 |
| 3,365,720 | 1/1968 | Kelleher | 343/837 |
| 3,375,361 | 3/1968 | Thompson et al. | 240/1.3 |
| 3,375,752 | 4/1968 | Fairbanks et al. | 88/24 |
| 3,428,397 | 2/1969 | Elmer | 355/11 |
| 3,498,714 | 3/1970 | Elmer | 355/70 |
| 3,560,729 | 2/1971 | Liberman | 240/9 |
| 3,663,083 | 5/1972 | Friedman et al. | 350/96 R |
| 3,763,348 | 10/1973 | Costello | 219/347 |
| 3,806,256 | 4/1974 | Ishak | 356/186 |
| 3,825,322 | 7/1974 | Mast | 350/236 |
| 3,920,311 | 11/1975 | Tsuda et al. | 350/89 |
| 3,923,381 | 12/1975 | Winston | 350/293 |
| 3,957,031 | 5/1976 | Winston | 126/270 |
| 4,002,499 | 1/1977 | Winston | 136/206 |
| 4,003,638 | 1/1977 | Winston | 350/293 |
| 4,006,355 | 2/1977 | Shemitz et al. | 240/51.11 |
| 4,027,151 | 5/1977 | Barthel | 240/41.35 R |
| 4,045,246 | 8/1977 | Mlavsky et al. | 136/89 PC |
| 4,095,905 | 6/1978 | Kuni et al. | 356/200 |
| 4,220,982 | 9/1980 | Martino | 362/97 |
| 4,223,346 | 9/1980 | Neiheisel et al. | 358/106 |
| 4,287,554 | 9/1981 | Wolff | 362/218 |

(List continued on next page.)

FOREIGN PATENT DOCUMENTS 57-19712A 2/1982 Japan .
59-123980A 7/1984 Japan .
2142444A 1/1985 United Kingdom .

OTHER PUBLICATIONS

LaMuth, "Measurements on Lambertain Objects: Some Novel Approaches", *Applied Optics*, vol. 14, No. 5, May 1975, pp. 1150–1155.
Advertisement, "High Irradiance Reflectors", Vortek Industries Ltd. (2 pgs.), Dec. 12, 1990.

(List continued on next page.)

*Primary Examiner*—William L. Sikes
*Assistant Examiner*—Robert E. Wise
*Attorney, Agent, or Firm*—Myers, Rose & Liniak

[57] ABSTRACT

An illumination system particularly useful for inspecting a workpiece by an optic scanner includes darkfield illumination produced mainly by two elongate light sources each having a reflector focussing member and a lenticular lens sheet spreading the light from its light source over its reflector focussing member to produce an approximate image of its light source on the line to be scanned. The illumination system further includes brightfield illumination produced mainly by a third elongate light source mounted laterally of the scanner optic axis, a refractive focussing member, and a further lenticular lens sheet producing an approximate image of the third light source on the line to be scanned. A beamsplitter aligned with the scanner optic axis reflects the light from the refractive focussing member towards the workpiece, and conducts therethrough both the darkfield and brightfield illumination reflected from the workpiece to the optic scanner.

20 Claims, 2 Drawing Sheets

U.S. PATENT DOCUMENTS

| | | | |
|---|---|---|---|
| 4,319,847 | 3/1982 | Howarth | 356/431 |
| 4,320,442 | 3/1982 | McCamy | 362/301 |
| 4,360,275 | 11/1982 | Louderback | 356/446 |
| 4,421,410 | 12/1983 | Karasaki | 356/378 |
| 4,423,470 | 12/1983 | Naito et al. | 362/17' |
| 4,441,817 | 4/1984 | Pryor | 356/375 |
| 4,449,818 | 5/1984 | Yamaguchi et al. | 356/237 |
| 4,460,942 | 7/1984 | Pizzuti et al. | 362/217 |
| 4,464,050 | 8/1984 | Kato et al. | 356/237 |
| 4,498,742 | 2/1985 | Uehara | 350/523 |
| 4,500,202 | 2/1985 | Smyth | 356/237 |
| 4,506,152 | 3/1985 | Gupta | 250/216 |
| 4,531,180 | 7/1985 | Hernandez | 362/297 |
| 4,555,727 | 11/1985 | Nun et al. | 358/106 |
| 4,597,665 | 7/1986 | Galbraith et al. | 356/237 |
| 4,661,706 | 4/1987 | Messerschmidt et al. | 250/341 |
| 4,692,690 | 9/1987 | Hara et al. | 324/73 PC |
| 4,693,601 | 9/1987 | Dabelstein et al. | 356/237 |
| 4,710,638 | 12/1987 | Wood | 250/492.1 |
| 4,714,327 | 12/1987 | Marshall | 350/504 |
| 4,718,767 | 1/1988 | Hazama | 356/381 |
| 4,730,895 | 3/1988 | Siedband et al. | 350/96.24 |
| 4,795,911 | 1/1989 | Kohno et al. | 250/572 |
| 4,801,810 | 1/1989 | Koso | 250/572 |
| 4,815,858 | 3/1989 | Snail | 356/446 |
| 4,821,114 | 4/1989 | Gebhardt | 358/75 |
| 4,824,194 | 4/1989 | Karasawa | 350/96.10 |
| 4,859,064 | 8/1989 | Messerschmidt et al. | 356/446 |
| 4,881,802 | 11/1989 | Stankewitz | 350/525 |
| 4,922,107 | 5/1990 | Rabl et al. | 250/504 |
| 4,933,817 | 6/1990 | Mochizuki et al. | 362/33 |
| 4,938,555 | 7/1990 | Savage | 350/96.18 |

OTHER PUBLICATIONS

Snail, "Reflectometer Design Using Nonimaging Optics", (draft; copy in file history of U.S. Pat. No. 4,815,858 to Snail, issued Mar. 23, 1989).

Brandenberg, "Focusing Properties of Hemispherical and Ellipsoidal Mirrors Reflectometers", J. Opt. Sci. Am., vol. 54, 10 (Oct. 1964) (incomplete copy).

Jacquez et al., "An Integrating Sphere for Measuring Diffuse Reflectance in the Near Infrared", *J. Opt. Sci. Am.*, vol. 45, No. 10, (Oct. 1955), pp. 781–785.

Gindele et al. "Spectral Reflectance Measurements Using an Integrating Sphere in the Infrared", *Applied Optics*, vol 24, No. 12, (Jun., 1985), pp. 1757–1760.

Edwards et al., "Integrating Sphere for Imperfectly Diffuse Samples", *Applied Optics*, vol. 51, (Nov. 1961), pp. 1279–1288, (incomplete copy).

ILLUMINATION SYSTEM AND INSPECTION APPARATUS INCLUDING SAME

RELATED APPLICATION

This patent application is for a continuation-in-part of our patent application Ser. No. 07/370,064 filed June 21, 1989, which in turn is a continuation of Ser. No. 07/150,332 filed Jan. 29, 1988, now abandoned.

FIELD AND BACKGROUND OF THE INVENTION

The present invention relates to inspection apparatus for optically inspecting the surface of a workpiece, and also to a surface illumination system for such inspection apparatus. The invention is particularly useful in a system for the high speed, automated, optic inspection of printed circuit boards, wafers and the like, for detecting faults which require reworking, and therefore the invention is described below with respect to this application, but it will be appreciated that the invention, or features thereof, could advantageously be used in other applications as well.

The conventional inspection apparatus for optically inspecting the surface of a workpiece, such as a printed circuit board or wafer, in order to detect faults typically includes a memory for storing reference data relating to the desired features of the workpiece surface, an illumination system for illuminating the workpiece surface, an optic sensor for sensing the light reflected from the illuminated workpiece surface and for outputting electric signals corresponding thereto, and a processor including logic circuitry for analyzing the electric signals outputted by the optic sensor for comparing them with the data stored in the memory, and for providing an indication of any discrepancies with respect thereto indicating a defect in the inspected workpiece surface. The reference data relating to the desired features of the workpiece surface to be compared with the sensed workpiece surface, may be in the form of stored images of the desired workpiece surface, or of stored design rules for the design of such workpiece surface.

Since the workpiece surfaces are not perfectly flat, but rather exhibit some degree of surface relief such as grooves, scratches, or angled surfaces, it would be desirable that the illumination system include a "Lambertian" diffuser, namely a perfect diffuser effective to cause the intensity of reflected radiation to be independent of direction. Such a diffuser would produce spatial uniformity of the light (i.e., a uniform "sky of illumination") above the workpiece and thereby eliminate shadows caused by the relief in the workpiece surface. However, Lambertian diffusers are extremely wasteful of light, and therefore such a diffusing surface would require an extremely intense light source and extremely high power, or would substantially slow-down the operation of the inspection apparatus in order to obtain workable signals having the required signal-to-noise ratio.

Our prior U.S. patent application Ser. No. 07/370,064 filed June 21, 1989 (which is a continuation of application Ser. No. 07/150,332 filed Jan. 28, 1988, and is based on Israel Patent Application 81459 filed Feb. 2, 1987) discloses an illumination system particularly useful for an optic inspection apparatus, which system provides what may be termed "Quasi-Lambertian" illumination. More particularly, that patent application describes an illumination system for optic scanners comprising darkfield illumination means, and combined brightfield-darkfield illumination means for illuminating a line to be scanned on the surface of the workpiece to be inspected. The darkfield illumination means comprises first and second light guides producing, at their output ends, elongate, narrow light sources extending parallel to and on opposite sides of the line to be scanned; and a beam concentrator for each of the light guides located to produce an at least approximate image of its respective light source on the line to be scanned on the surface of the workpiece. Each of the beam concentrators further includes a reflector focussing member and an aberration plate for slightly defocussing or diffusing the image of its respective light source on the line to be scanned. In addition, the brightfield illumination means also include a light guide producing, at its output end, an elongate, narrow light source, and a reflector focussing member and aberration plate for producing an approximate image of its respective light source on the line to be scanned.

Illumination systems constructed in accordance with the system illustrated in our prior application Ser. No. 07/150,332 have been found to be highly effective in eliminating shadows caused by the relief in the workpiece surface, while at the same time to be very economical in the power required and in the light produced, such that the inspection apparatus can be operated at a substantially high speed while still obtaining workable signals having the required signal-to-noise ratio.

An object of the present invention is to provide an improved illumination system of the foregoing type which enables the system to be considerably miniaturized so as to take up a small fraction of the space of the system described as a preferred embodiment in our patent application Ser. No. 07/370,064. Another object of the present invention is to provide an improved illumination system of the foregoing type in which the solid angle of illumination is considerably increased as compared to the system described as a preferred embodiment in the above-identified patent application.

According to the present invention, there is provided an illumination system for optic scanners as described in our patent application Ser. No. 07/370,064, wherein the darkfield illumination means comprises an elongate lenticular lens sheet (instead of an aberration plate) between each of the first and second light sources and their respective reflector focussing members effective to spread the light over their respective reflector focussing members.

Each lenticular lens sheet is one having an array of cylinder lenses aligned perpendicularly to its respective narrow light source. The use of such an array of cylinder lenses, rather than a conventional aberration plate such as a ground glass diffuser, enhances the light efficiency of the system. By aligning the cylindrical lenticles perpendicularly to the light source, the light spreading is effected only along the axis of the cylinder focussing elements, and thereby better ensures adequate angular coverage around an axis perpendicular to the scanned line.

According to further features in the preferred embodiment of the invention described below, the brightfield illumination means comprises a third light source mounted laterally of the optic axis; a refractive (instead of reflective) focussing member for producing an approximate image of the third light source on the line to be scanned on the surface of the workpiece; another lenticular lens sheet for spreading the light from the third light source over the refractive focussing member; and a beamsplitter aligned with the optic axis for reflecting the light from the focussing member towards the workpiece, and for conducting therethrough both the darkfield and brightfield illumination reflected from the workpiece to the optic scanner.

According to still further features in the described preferred embodiment, each of the reflector focussing members is a concave reflector which subtends an arc of 50°-60° (preferably about 50°) on each side of the optic axis, and the two reflector focussing members are spaced from each other 2°-10° (preferably about 5°) on each side of the optic axis.

An illumination system constructed in accordance with the foregoing features has enabled the system to be miniaturized such as to occupy a space of only about one-fifth that of the commercial form of the system described as a preferred embodiment in our prior patent application Ser. No. 07/370,064. Such system also provides a considerably larger solid angle of illumination, i.e., about 110°, as compared to about 60° in the commercial form of that system.

The present invention also provides inspection apparatus for optically inspecting the surface of a workpiece, comprising an illumination system as described above for illuminating the surface of the workpiece. Such inspection apparatus also comprises a memory for storing data relating to the desired features on the workpiece surface; an optic sensor for sensing the light reflected from the illuminated workpiece surface and for outputting electrical signals corresponding thereto; and a processor including logic circuitry for analyzing the electric signals outputted by the optic sesnor, for comparing them with the data stored in the memory, and for providing an indication of the discrepancies with respect thereto indicating a defect in the inspected workpiece surface.

When an illumination system as described above is used in such inspection apparatus, the objective lens of the optic inspecting system may be much more closely located with respect to the workpiece. This greatly simplifies the lens design, and also effects substantial savings in the light and power requirements in order to obtain the necessary signal-to-noise ratio for any scanning speed.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF A PREFERRED EMBODIMENT

Overall Inspection System

Figure 1:
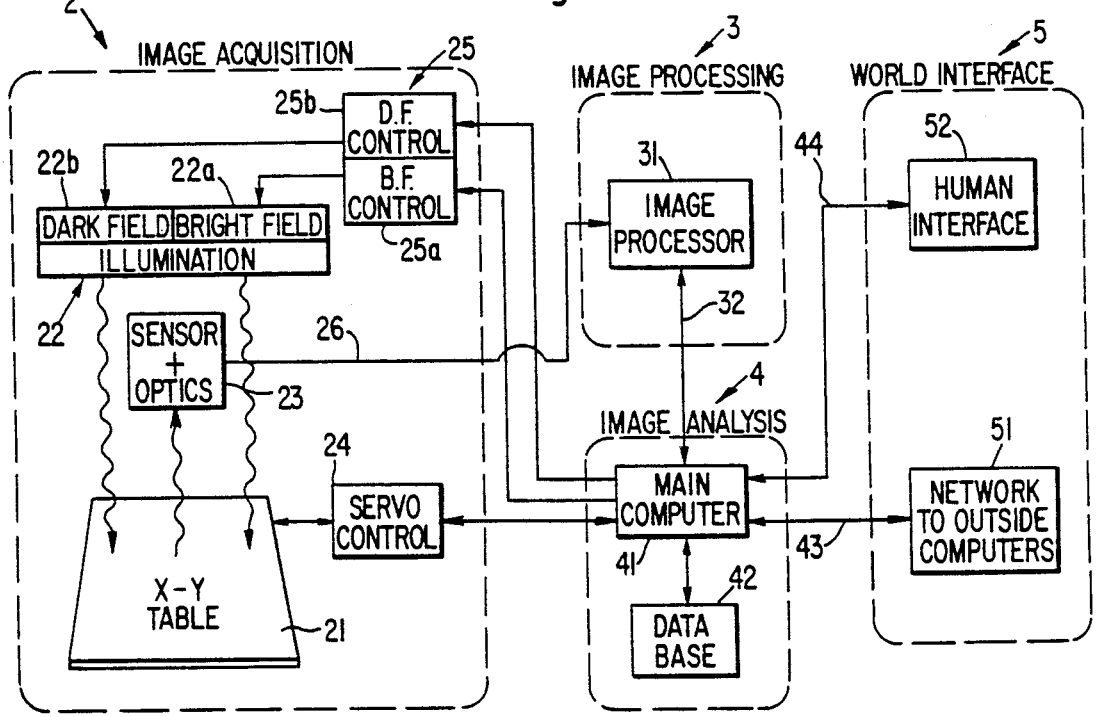
FIG. 1 is a block diagram illustrating one form of inspection apparatus constructed in accordance with the present invention for optically inspecting the surface of a workpiece, particularly a printed circuit board or wafer.

The overall automatic inspection system illustrated in FIG. 1 is intended for optically inspecting the surface of printed circuit boards, wafers, or like devices in order to detect flaws in the surface. Briefly, the illustrated system includes the following subsystems: an image acquisition subsystem, generally designated 2; an image processing subsystem, generally designated 3; an image analysis subsystem, generally designated 4; and a world interface subsystem, generally designated 5.

The function of the image acquisition subsystem 2 is to illuminate and scan the workpiece, and to transfer an image of the scanned part to the image processing subsystem 3. Thus, the image acquisition subsystem 2 includes an X-Y table 21 adapted to receive the workpiece to be inspected; an illumination unit 22 for illuminating the workpiece on the table 21; a sensor/optic unit 23 for scanning the illuminated workpiece and for optically sensing its image; and a servo-control unit 24 for moving table 21 along two orthogonal axes in order to sense the complete surface of the workpiece.

The illumination unit 22 includes a brightfield light producing means 22a, and a darkfield light producing means 22b. A control unit, generally designated 25, includes a brightfield control 25a for controlling the intensity of the brightfield illumination, and a separate darkfield control 25b for controlling the intensity of the darkfield illumination.

The output from the sensor/optic unit 23 of the image acquisition system 2, appears on output line 26 applied to the image processing subsystem 3.

The image processing subsystem 3 includes an image processor 31 whose function is to process the image and to segment it reliably into functional areas. Thus, when the workpiece is a printed circuit board, image processor 31 segments the output, appearing on line 26 from the image acquisition subsystem 2, into the functional areas of conductors and dielectric substrate. Image processor 31 is a special purpose hardware unit with dedicated software aimed at enhancing the image and segmenting it into its functional areas. The output from image processor 31 is applied via bus 32 to the image analysis subsystem 4.

The function of the image analysis subsystem 4 is to find all flaws in the segmented image, based on various algorithms. It includes a main computer 41 having logic circuitry for analyzing the electric signals outputted by the image processor 31, and for comparing them with the data stored in the memory of the database unit 42 for providing an indication of any discrepancies resulting from a defect in the inspected workpiece surface. The main computer 41 implements the flaw detection and flaw reporting algorithms, and effects the comparison with the reference images stored in the database 42 in order to determine whether a flaw exists, and if so, to indicate its location, and thereby to enable the workpiece to be reworked to correct the flaw. As indicated earlier, the database 42 may store image data and/or design rules with respect to which the sensed workpiece data are to be compared.

The main computer 41 in the image analysis subsystem 4 also controls the brightfield control unit 25a, the darkfield control unit 25b, the servo-control unit 24, and the image processor 31. Its output is fed to the world interface subunit 5 via output buses 43 and 44.

Output bus 43 from the image analysis subsystem 4 is applied to a network unit 51 in the world interface subsystem 5. Network unit 51 is a package of hardware and software allowing communication with outside computers. The world interface subsystem 5 further includes a human interface unit 52, e.g., monitors permitting the operator to monitor the data outputted from the main computer, and also a keyboard or other input device permitting intervention by the operator.

Except for the illumination unit 22 in the image acquisition subsystem 2 of FIG. 1, the overall system illustrated in FIG. 1 is well known and in commercial use, and therefore further details of the construction and operation of the system are not set forth herein. The illumination unit 22 is based on the system described in the above-cited patent application Ser. No. 07/370,064, but includes a number of improvements as shown in FIG. 2 and as described more particularly below.

The Improved Illumination Unit 22

Figure 2:
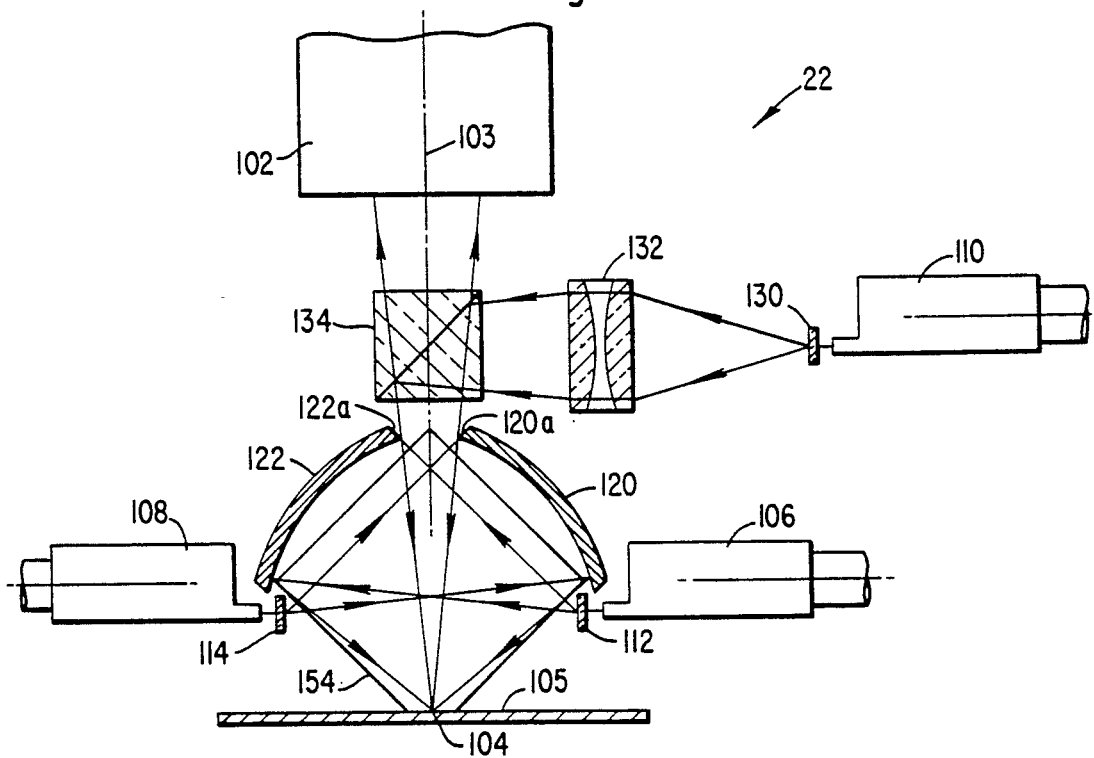
FIG. 2 is an optic diagram illustrating the illumination system of the present invention.
Figure 3:
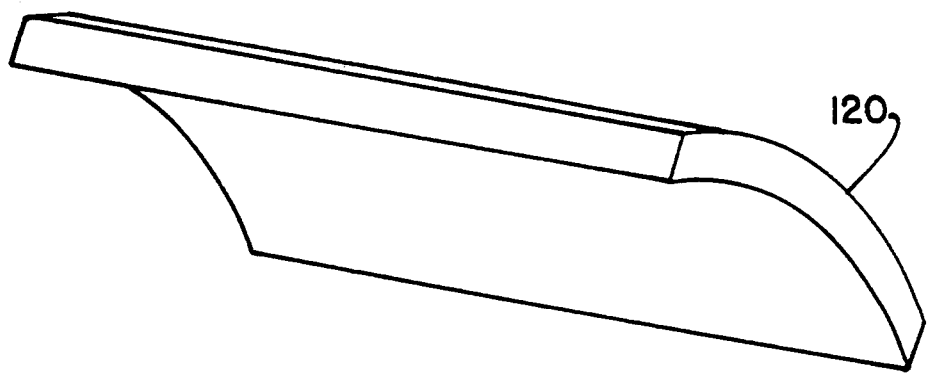
FIG. 3 is a perspective view of a reflector as illustrated in FIG. 2.

The optic diagram illustrated in FIG. 2 is a schematic cross-section of the improved illumination unit 22 in a direction perpendicular to the direction of the line shaped area that is sensed by the objective lens 102 of the line-scan camera. The optic axis 103 of the objective lens 102 intersects, at point 104, the surface of the workpiece 105 to be scanned.

Illumination unit 22 comprises three flat fiber optic light guides 106, 108 and 110. Light guides 106 and 108 provide most of the darkfield illumination of the scanned line, whereas light guide 110 provides the brightfield illumination of the scanned line, as well as part of the darkfield illumination.

The light guides 106, 108 and 110, and the lamps feeding the light at their input ends, may be as illustrated in our prior application Ser. No. 07/370,064. As described in that patent application, the two darkfield light guides 106, 108 produce, at their output ends, elongate, relatively narrow light sources extending in spaced relation substantially parallel to and on opposite sides of the scanning line passing through the optic axis 103; and a beam concentrator, in the form of a concave reflector focussing member 120, 122, is provided for each light guide and is located relative thereto to produce an approximate image of its respective light source on the line to be scanned. Each of the two focussing reflectors 120, 122 is defined by the generatrix of a cylinder, preferably an elliptical cylinder.

As distinguished from the construction described in that patent application, a lenticular lens sheet 112, 114, is provided at the output end of each light guide 106, 108, instead of an aberration plate as described in that patent application. The lenticular lenses 112, 114 spread the light from the output ends of the light guides 106, 108 over the inner surfaces of the focussing reflectors 120, 122. The concave surfaces of the reflectors face the lenticular lenses and the workpiece 105, and are effective to produce an approximate image of the linear light sources on the surface of the workpiece.

As indicated earlier, the use of a lenticular lens sheet having a plurality of cylinder lenses aligned perpendicularly to the light source, rather than a conventional diffuser-type aberration plate, enhances the light efficiency of the system. By aligning the cylindrical lenticles vertically in FIG. 2, the light spreading is effected only along the axis of the cylinder focussing elements, i.e., in a direction normal to the plane of FIG. 2. This additional spreading better ensures adequate angular coverage around an axis perpendicular to the scanned line. The angular coverage around the scanned line itself is ensured by the focussing action of the focussing elements.

Each of the two reflectors 120, 122 subtends an arc of 40°–60° on each side of the optic axis 103, and their inner edges 120a, 122a are spaced from each other about 2°–10° on each side of the optic axis 103. Preferably, each reflector 120, 122 is spaced about 5° from the optic axis 105 and subtends an arc of about 50°, thereby providing a solid angle of illumination of about 110°.

The brightfield illumination light guide 110 also includes a lenticular lens 130 at its output end, which uniformly spreads the light to a refractive focussing member in the form of a cylindrical lens 132. Lens 132 substantially focusses the light via a beamsplitter 134 onto the scanning line on the surface of the workpiece 105.

Beamsplitter 134 is of the prismatic type and is aligned with the optic axis 103 of the objective lens 102. It reflects the substantially focussed light from the brightfield light guide 110 and cylindrical lens 132 onto the workpiece 105, and transmits both the brightfield light and darkfield light from workpiece 105 to the objective lens 102 of the optic scanner.

As described in our prior application Ser. No. 07/370,064, a pair of planar reflectors 154 are provided at the ends of the light guides 106, 108, and extend substantially perpendicularly to the illuminated workpiece surface 105, to compensate for the light fall-off at the ends of the illuminated line. The end reflectors 154 are mounted flush with the ends of the light guides 106, 108, with the reflecting sides facing inwardly, and with their bottom edges as close as possible to the illuminated workpiece surface 105. The planar reflectors 154 act to optically extend the length of the illumination system along the scanned line, thereby ensuring a uniform angular coverage at each point along the scanned line.

An illumination system as illustrated in FIG. 2 greatly reduces the space required for the system, to about one-fifth that in the present commercial form of the system constructed in accordance with our prior application Ser. No. 07/370,064. It also provides a much larger solid angle of illumination, about 110° as compared to about 60° in the commercial system. Such an arrangement thus permits the objective lens 102 to be located much closer to the workpiece 105. This greatly simplifies the lens design, and also effects substantial savings in the light and power requirements in order to obtain the necessary signal-to-noise ratio for any scanning speed.

While the invention of this application has been described with respect to one preferred embodiment, it will be appreciated that many variations, modifications and other applications may be made.

What is claimed is:

1. An illumination system for an optic scanner particularly useful for illuminating a line to be scanned on the surface of a workpiece and aligned with the scanner optic axis, comprising:

darkfield illumination means and brightfield illumination means for illuminating the line to be scanned;
said darkfield illumination means comprising first and second light guides producing, at their output ends, elongate, narrow light sources extending parallel to and on opposite sides of the line to be scanned; and a beam concentrator for each of said light guides located to produce an approximate image of its respective light source on the line to be scanned on the surface of the workpiece;

each of said beam concentrators including a reflector focussing member and a lenticular lens sheet between its respective light source and reflector focussing member effective to spread the light over its respective reflector focussing member.

2. The illumination system according to claim 1, wherein each of said lenticular lens sheets includes an array of cylinder lenses aligned perpendicularly to the respective narrow light source.

3. The illumination system according to claim 2, wherein said beamsplitter of said brightfield illumination means is a prismatic beamsplitter.

4. The illumination system according to claim 1, wherein said brightfield illumination means comprises:
a third light source mounted laterally of the scanner optic axis;
a refractive focussing member for producing an approximate image of said third light source on the line to be scanned on the surface of the workpiece;
another lenticular lens for spreading the light from said third light source over said refractive focussing member;
and a beamsplitter aligned with said optic axis for reflecting the light from said focussing member towards said workpiece, and for conducting therethrough both the darkfield and brightfield illumination reflected from the workpiece to the optic scanner.

5. The illumination system according to claim 1, wherein each of said reflector focussing members is a concave reflector defined by the generatrix of a cylinder.

6. The illumination system according to claim 5, wherein said concave reflectors each subtends an arc of 40°-60° on each side of the optic axis, and are spaced from each other 2°-10° on each side of the optic axis.

7. The illumination system according to claim 5, wherein said concave reflectors each subtends an arc of approximately 50° on each side of the optic axis, and are spaced from each other approximately 5° on each side of the optic axis.

8. The illumination system according to claim 1, wherein each of said concave reflectors is defined by the generatrix of an elliptical cylinder.

9. An illumination system for optic scanners particularly useful for illuminating a line on the surface of a workpiece to be scanned, comprising:
first and second light guides producing, at their output ends, elongate, narrow light sources extending parallel to and on opposite sides of the line to be scanned on the surface of the workpiece;
a concave light reflector for each of said light guides effective to approximately focus said light sources on the line to be scanned, each of said light reflectors subtending an arc of approximately 40°-60° on each side of the optic axis and being spaced from each other about 2°-10° on each side of the optic axis; and
a lenticular lens sheet between each of said first and second light sources and their respective concave reflectors and effective to spread the light from the light sources substantially uniformly over their respective reflectors; each of said lenticular lens sheets including an array of cylindrical lenses aligned perpendicularly to the respective narrow light source.

10. The illumination system according to claim 9, further comprising:
a third light source mounted laterally of said optic axis;
a refractive focussing member for producing an at least approximate image of said third light source on said line to be scanned on the surface of the workpiece;
a lenticular lens for spreading the light from said third light source over said refractive focussing member;
and a beamsplitter aligned with said optic axis for reflecting the light from said refractive focussing member towards said workpiece, and for conducting therethrough the light reflected from the workpiece to the optic scanner.

11. The illumination system according to claim 9, wherein each of the concave reflectors subtends an arc of 40°-60° on each side of the optic axis, the two reflectors being spaced from each other 2°-10° on each side of the optic axis.

12. The illumination system according to claim 11, wherein said concave reflectors each subtends an arc of about 50° and are spaced from each other about 5° on each side of the optic axis.

13. The illumination system according to claim 9, wherein said first and second light guides are fiber-optic light guides.

14. The illumination system according to claim 9, wherein said concave reflectors are defined by the generatrix of an elliptical cylinder.

15. Inspection apparatus for optically inspecting the surface of a workpiece, comprising:
a memory for storing data relating to the desired features of the workpiece surface;
an illumination system according to claim 1 for illuminating the surface of the workpiece;
an optic sensor for sensing the light reflected from the illuminated workpiece surface, and for outputting electrical signals corresponding thereto;
and a processor including logic circuitry for analyzing the electric signals outputted by said optic sensor, for comparing them with the data stored in said memory, and for providing an indication of the discrepancies with respect thereto indicating a defect in the inspected workpiece surface.

16. Inspection apparatus according to claim 15, wherein the brightfield illumination system means comprises: a third light source mounted laterally of the scanner optic axis; a refractive focussing member for producing an approximate image of the third light source on the line to be scanned on the surface of the workpiece; another lenticular lens for spreading the light from the third light source over the refractive focussing member; and a beamsplitter aligned with the optic axis for reflecting the light from the lenticular lens towards the workpiece, and for conducting therethrough both the darkfield and brightfield illumination reflected from the workpiece to the optic scanner.

17. Inspection apparatus according to claim 15, wherein the first and second light guides are fiber-optic light guides.

18. Inspection apparatus according to claim 15, wherein each of the concave reflectors is defined by the generatrix of an elliptical cylinder.

19. Inspection apparatus according to claim 15, wherein the concave reflectors each subtends an arc of 40°-60° on each side of the optic axis, and are spaced from each other 2°-10° on each side of the optic axis.

20. Inspection apparatus according to claim 15, wherein the beamsplitter of the brightfield illumination means is a prismatic beamsplitter.

* * * * *